United States Patent
Barreau et al.

(10) Patent No.: US 9,750,831 B2
(45) Date of Patent: Sep. 5, 2017

(54) DECONTAMINATION DEVICE FOR MEDICAL MATERIAL

(71) Applicant: L.B.A. CONSULTING, Saint-Fargeau (FR)

(72) Inventors: Christophe Barreau, Treigny (FR); Eric Bertrand, Seignelay (FR); Philippe Macaire, Dubai (AE); Jean-Paul Carprieaux, Avernes (FR)

(73) Assignee: L.B.A. CONSULTING, Saint-Fargeau (FR)

( * ) Notice: Subject to any disclaimer, the term of this patent is extended or adjusted under 35 U.S.C. 154(b) by 0 days.

(21) Appl. No.: 14/897,377

(22) PCT Filed: Jun. 10, 2014

(86) PCT No.: PCT/FR2014/051375
§ 371 (c)(1),
(2) Date: Dec. 10, 2015

(87) PCT Pub. No.: WO2014/199058
PCT Pub. Date: Dec. 18, 2014

(65) Prior Publication Data
US 2016/0129141 A1   May 12, 2016

(30) Foreign Application Priority Data
Jun. 10, 2013   (FR) ...................... 13 55335

(51) Int. Cl.
*B01J 19/00* (2006.01)
*A61L 2/10* (2006.01)
*A61L 2/22* (2006.01)
*A61L 2/18* (2006.01)
*A61L 2/20* (2006.01)

(52) U.S. Cl.
CPC ....... *A61L 2/10* (2013.01); *A61L 2/18* (2013.01); *A61L 2/20* (2013.01); *A61L 2/22* (2013.01); *A61L 2202/24* (2013.01)

(58) Field of Classification Search
CPC ................. A61L 2/10; A61L 2/18; A61L 2/22
USPC ........................................ 422/291
See application file for complete search history.

(56) References Cited

U.S. PATENT DOCUMENTS

| 4,029,967 A | 6/1977 | Tetzlaff |
| 5,571,488 A * | 11/1996 | Beerstecher ......... A61C 19/002 134/94.1 |
| 2004/0091389 A1 | 5/2004 | Malkin et al. |

(Continued)

OTHER PUBLICATIONS

International Search Report dated Oct. 13, 2014 from corresponding International Patent Application No. PCT/FR2014/051375; 3 pgs.

*Primary Examiner* — Kevin Joyner
(74) *Attorney, Agent, or Firm* — Maier & Maier, PLLC

(57) ABSTRACT

A decontamination device for medical material, including a support intended to receive and hold said medical material to be decontaminated on a predefined axis, a spraying means, a drying means and an irradiating means, wherein said spraying means is mounted in rotation about said predefined axis and in translation parallel to said predefined axis, in such a way that the spraying is directed towards said predefined axis, said drying means is mounted in translation parallel to said predefined axis, and said irradiating means is mounted in translation parallel to said predefined axis.

10 Claims, 2 Drawing Sheets

(56) References Cited

U.S. PATENT DOCUMENTS

| | | |
|---|---|---|
| 2009/0020135 A1 | 1/2009 | Adams |
| 2009/0314308 A1* | 12/2009 | Kim ..................... A61L 2/0047 134/1 |
| 2010/0183476 A1* | 7/2010 | Lu ............................ A61L 2/10 422/21 |
| 2011/0044848 A1* | 2/2011 | Wright ..................... A61L 2/10 422/24 |
| 2012/0107184 A1 | 5/2012 | Asiyanbola et al. |

* cited by examiner

DECONTAMINATION DEVICE FOR MEDICAL MATERIAL

TECHNICAL FIELD

The invention relates to the field of decontamination of medical devices and preferentially the decontamination of laryngoscope handles.

PRIOR ART

Medical devices are available in disposable or reusable forms. It is particularly of interest to use disposable material to ensure optimal asepsis and prevent the transmission of micro-organisms from one patient to another. However, not all medical devices can be produced in the form of disposable material. Furthermore, the lack of tightness of some of these devices and the presence of batteries does not allow the cleaning thereof by soaking.

The laryngoscope is a medical instrument essentially used for tracheal intubation making it possible to view the glottis. It consists of two parts:

a blade used to clear the tongue, soft palate and epiglottis, this blade may be single-use, a handle used for handling the instrument. It contains batteries and, in the case of fibre optic laryngoscopes, the light source. This portion of the laryngoscope is reusable and must be cleaned between each use.

According to an article of the British Journal of Anaesthesia (Young et al. November 2011), it is recommended that laryngoscope handles be sterilised between each use, but only 22% of hospital departments autoclave laryngoscope handles between each use. At the present time, there is no clear protocol for this decontamination. In this study, 40% of the "clean" laryngoscope handles analysed were contaminated with microbes.

Usually, the decontamination method consists of using disposable wipes impregnated with a decontamination liquid before and after each use of the laryngoscope handle. However, this method is not totally satisfactory as it is dependent on the operator performing the decontamination and it is particularly lengthy. Furthermore, laryngoscope handles have rough areas wherein fibres may be retained and which are difficult to clean thoroughly.

One study conducted by the applicants demonstrated that, out of a sample of 25 laryngoscope handles, 4 were still contaminated after the usual decontamination procedure. Of the contaminants isolated, mention may be made of *Staphylococcus aureus*, pyocyanic *bacillus, Klebsiella Pneumoniae* and *E. Coli*.

The present invention relates to a device for decontaminating medical devices and more particularly laryngoscope handles. The present invention makes it possible to solve the problems associated with the methods of the prior art. More particularly, the device according to the invention enables rapid, automated and total decontamination of medical devices.

SUMMARY OF THE INVENTION

As such, the present invention relates in particular to a decontamination device for medical material, comprising a support intended to receive and hold said medical material to be decontaminated on a predefined axis, a spraying means, a drying means and an irradiating means, characterised in that said spraying means is mounted in rotation about said predefined axis and in translation parallel to said predefined axis, in such a way that the spraying is directed towards said predefined axis, said drying means is mounted in translation parallel to said predefined axis, and said irradiating means is mounted in translation parallel to said predefined axis.

In the context of the present invention, the term "predefined axis" is intended to denote that, when the medical material to be decontaminated is placed on said support, it is held in a substantially constant position from one use to another and occupies substantially the space of a cylinder wherein the axis of symmetry coincides with said "predefined axis". As such, said "predefined axis" corresponds to the longitudinal axis of symmetry of the inner volume defined by the spraying means, drying means and irradiating means.

In the context of the present invention, "mounted in rotation about said predefined axis" is intended to denote that the means in question are movable in rotation about said predefined axis and/or that said support intended to receive and hold said medical material to be decontaminated on a predefined axis is mounted in rotation about said predefined axis and that said means in question are stationary.

In the context of the present invention, the term "parallel to said predefined axis" is intended to denote that the means in question are movable in translation parallel to said predefined axis and/or that said support intended to receive and hold said medical material to be decontaminated on a predefined axis is mounted in translation on said predefined axis and that the means in questions are stationary.

In the context of the present invention, the term "spraying means" refers to means capable of spraying a liquid.

In the context of the present invention, the term "irradiating means" refers to sources of radiation having wavelengths between 150 and 450 nm.

According to one preferred embodiment of the invention, said spraying means, said drying means and/or said irradiating means are included in a part forming a cylindrical passage, intended to receive said medical material to be decontaminated. In this case, said "predefined axis" is the longitudinal axis of symmetry of said cylinder.

According to one particularly preferred embodiment of the invention, said spraying means, said drying means and said irradiating means are included in one or two parts, arranged on the same longitudinal axis, forming a cylindrical passage, intended to receive said medical material to be decontaminated. In this case, said "predefined axis" is the longitudinal axis of symmetry of said cylinder.

According to one preferred embodiment of the invention, said irradiating means forms a cylinder arranged on the inner surface of said part.

According to one preferred embodiment of the invention, said drying means is also mounted in rotation about the predefined axis.

According to one preferred embodiment of the invention, said irradiating means is also mounted in rotation about the predefined axis.

According to one preferred embodiment of the invention, said drying means is a means capable of producing an air knife.

According to one preferred embodiment of the invention, said means capable of producing an air knife is arranged annularly about the predefined axis.

According to one preferred embodiment of the invention, said air knife is substantially perpendicular to the predefined axis.

In the last three embodiments, the use of an air knife makes it possible to dry the device but also to detach solid materials possibly placed on the surface thereof. This makes it possible to arrive at decontamination levels largely superior to those previously observed.

According to one preferred embodiment of the invention, said irradiating means is a source of UV and preferentially of UV-C.

According to a further particularly preferred embodiment, said irradiating means is a source capable of emitting sequentially or simultaneously radiation belonging to the UV-A, UV-B and UV-C range.

According to one preferred embodiment of the invention, said spraying means is a nebulisation means.

In the context of the present invention, the term "nebulisation means" is intended to denote any means suitable for converting a liquid solution into a mist of particles suspended in a gas.

DESCRIPTION OF EMBODIMENTS

Figures 1, 2:
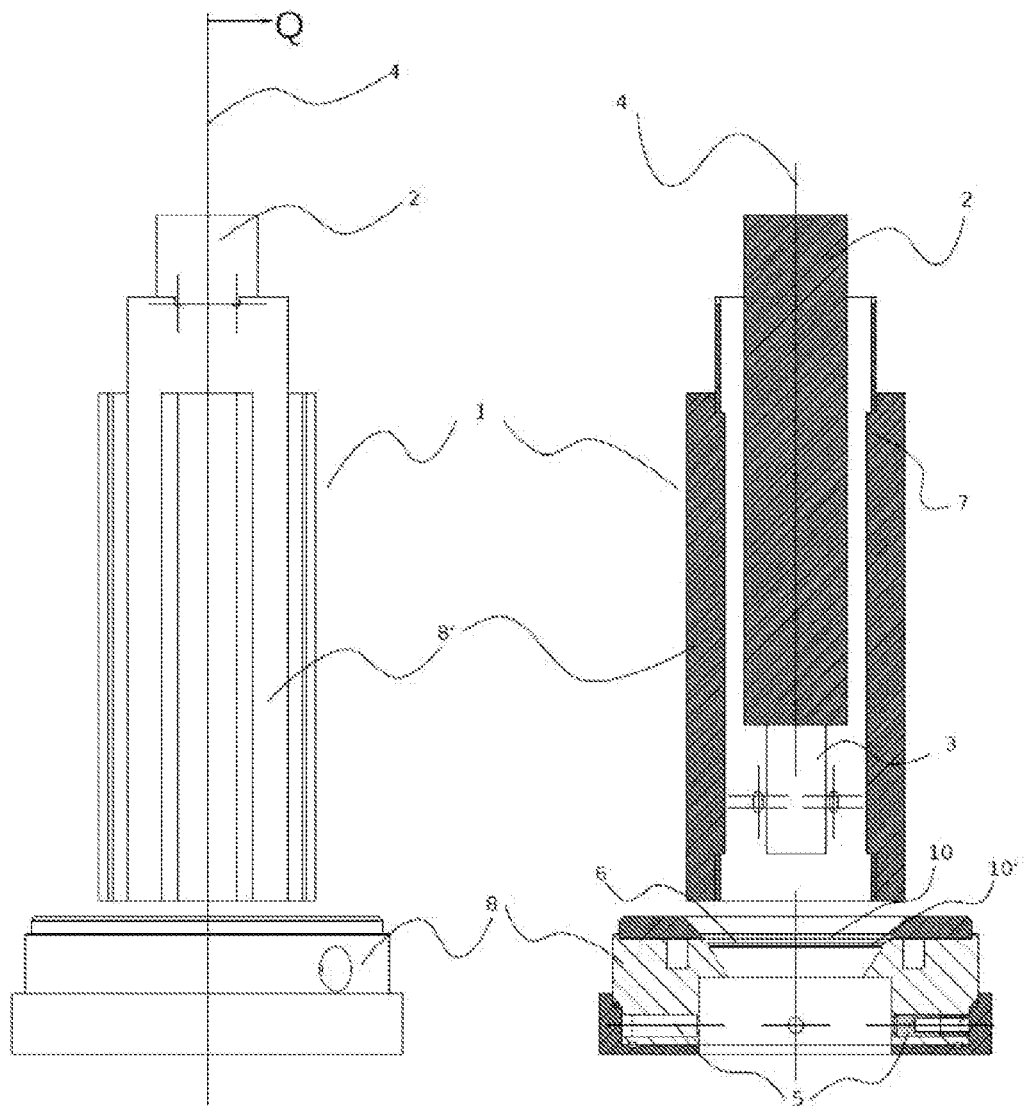
FIG. 1 shows a front view of an embodiment of a device according to the invention.
FIG. 2 is a sectional view of the same embodiment.
Figure 3:
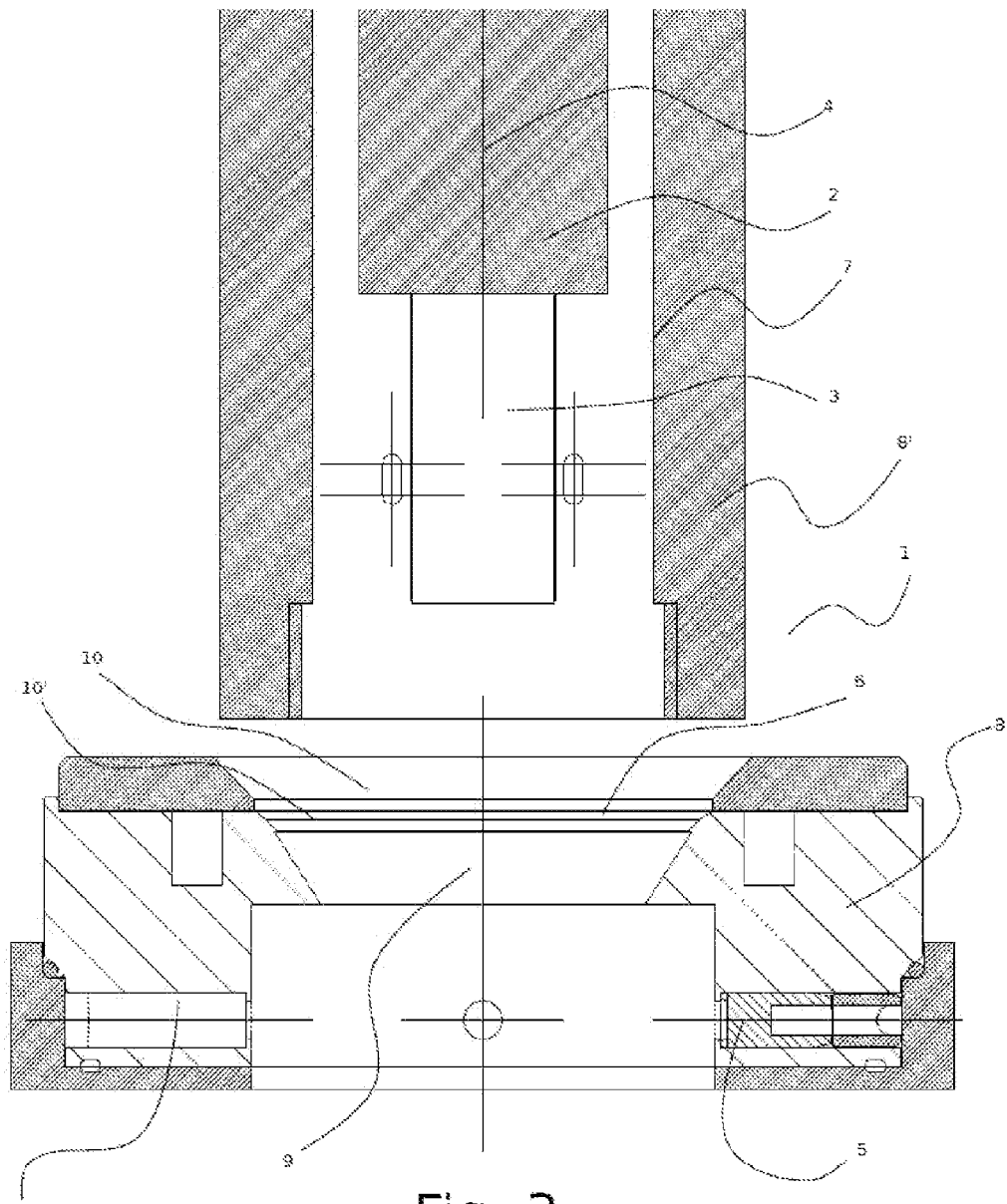
FIG. 3 shows a partial sectional view of the same embodiment.

With reference to FIGS. 1 and 2, the device 1 consists of a vertical column, comprising the various means 5, 6, 7 for decontaminating the medical material 2.

According to one preferred embodiment of the invention, said medical material 2 is chosen in the group comprising laryngoscope handles and probes.

The device 1 according to the invention is preferentially placed in an enclosure which may be completely closed. Said enclosure preferentially comprises an access hatch for placing the medical material 2 on the support 3 and for removing it from said support 3 at the end of the decontamination procedure.

The support 3 is preferentially associated with a means allowing the movement of said support 3 in translation and in rotation relative to the predefined axis 4. All the means included in the device 1 according to the invention are preferentially controlled automatically by an advantageously programmable control device (e.g. electronic board, computer).

The support 3 preferentially comprises a means for associating the support and the material to be decontaminated 2. This means may take any form, among the preferred means, mention may be made of threaded rods. Even more preferentially, said means is identical to the means for associating the laryngoscope handle and the blade intended to be used with said handle.

Once the material to be decontaminated 4 is fixed on the support 3, the enclosure is closed and the decontamination process is started up by the operator.

The material to be decontaminated 2 will move vertically with a rotation between 45° and 360°. Alternatively, the means for decontamination 5, 6, 7 move and the medical material to be decontaminated 2 remains stationary.

In a first phase, the medical device will move in a part 8 forming a cylindrical passage 9 comprising at least one spraying means 5 which will mist-spray a decontaminant solution on the entire surface.

According to one preferred embodiment of the invention, said decontaminant solution is chosen in the group comprising the liquids comprising acridine derivatives, aluminium derivatives, phenols and derivatives thereof, nitrofuran derivatives, iodine derivatives, quinoline derivatives, quaternary ammoniums, mercury derivatives, hydrogen peroxide, eosin, propanol, sodium tosylchloramide, isopropanol, potassium permanganate, sodium hypochlorite and ethanol.

According to one preferred embodiment of the invention, the spraying means 5 is connected to an enclosure containing said decontaminant solution. The flow of this solution via the spraying means will induce the nebulisation and distribution thereof on the entire surface of the material to be decontaminated 2. The propulsion of the decontaminant solution via the spraying means 5 is advantageously carried out by means of a pump.

In a second phase, the medical material 2 will move vertically, again rotating on itself in the part 8 and pass in front of the drying means 6 which will make it possible to remove the decontaminant solution.

This drying means 6 is preferentially a means capable of producing an air knife. It may particularly take the form of an annular opening, present on the inner surface of the part 8, advantageously connected to a compressed gas source and even more advantageously connected to the compressed air source of the hospital establishment receiving the device according to the invention. Preferentially, this annular opening comprises two lips 10, 10' capable of directing said air knife. Advantageously, said air knife passes through a trajectory forming an angle between 10° and 85° with said predefined axis. According to one more preferred embodiment, said angle is between 20° and 50°.

Then, the medical material 2 will be positioned, for a predefined time, at the centre of the part 8' comprising, on the inner surface, thereof an irradiating means 7. Said means is preferentially a source of UV-C radiation.

The medical material 2 then returns to the nominal position, ready to be used.

The invention claimed is:

1. A decontamination device for medical material comprising:
   a support intended to receive and hold said medical material to be decontaminated, a spraying mechanism, a drying mechanism and an irradiating mechanism, said drying mechanism and said irradiating mechanism further comprise a part forming a cylindrical passage, configured to receive said medical material to be decontaminated, wherein said spraying mechanism is configured to rotate about the longitudinal axis of symmetry of said cylindrical passage and in translation parallel to said axis of symmetry, in such a way that the spraying is directed towards said axis of symmetry, said drying mechanism produces an air knife and is mounted in translation parallel to said axis of symmetry, and said irradiating mechanism is mounted in translation parallel to said axis of symmetry, wherein the air knife passes through a trajectory forming an angle between 10° and 85° of said axis of symmetry.

2. The decontamination device for medical material according to claim 1, comprising:
   a support intended to receive and hold said medical material to be decontaminated, a spraying mechanism, a drying mechanism and an irradiating mechanism, said drying mechanism and said irradiating mechanism are included in a part forming a cylindrical passage, intended to receive said medical material to be decontaminated, characterised in that said support is mounted in rotation about the longitudinal axis of symmetry of said cylindrical passage and in translation on said axis of symmetry.

3. The decontamination device for medical material according to claim 1, wherein said irradiating mechanism forms a cylinder arranged on the inner surface of said annular part.

4. The decontamination device for medical material according to claim 1, wherein said drying mechanism is mounted in rotation about the axis of symmetry.

5. The decontamination device for medical material according to claim 1, wherein said irradiating mechanism is also mounted in rotation about the axis of symmetry.

6. The decontamination device for medical material according to claim 1, wherein said drying mechanism capable of producing an air knife is arranged annularly about the axis of symmetry.

7. The decontamination device for medical material according to claim 1, wherein said air knife is substantially perpendicular to the axis of symmetry.

8. The decontamination device for medical material according to claim 1, wherein said irradiating mechanism is a source of UV and preferentially of UV-C.

9. The decontamination device for medical material according to claim 1, wherein said irradiating mechanism is a source capable of emitting sequentially or simultaneously radiation belonging to the UV-A, UV-B and UV-C range.

10. The decontamination device for medical material according to claim 1, wherein said spraying mechanism is a nebulisation means.

\* \* \* \* \*